US006500469B1

(12) United States Patent
Preuss et al.

(10) Patent No.: US 6,500,469 B1
(45) Date of Patent: Dec. 31, 2002

(54) METHODS AND COMPOSITIONS FOR REDUCING CHOLESTEROL LEVELS USING A PROANTHOCYANIDIN AND NIACIN-BOUND CHROMIUM COMPLEX

(75) Inventors: Harry G. Preuss, Fairfax Station, VA (US); Debasis Bagchi, Concord, CA (US)

(73) Assignee: Dry Creek Nutrition, Inc., Modesto, CA (US)

( * ) Notice: Subject to any disclaimer, the term of this patent is extended or adjusted under 35 U.S.C. 154(b) by 0 days.

(21) Appl. No.: 09/838,995

(22) Filed: Apr. 20, 2001

Related U.S. Application Data

(60) Provisional application No. 60/199,076, filed on Apr. 20, 2000.

(51) Int. Cl.$^7$ .......................... A61K 35/78; A61K 9/00
(52) U.S. Cl. ...................... 424/766; 424/400; 424/725
(58) Field of Search ................ 424/766, 400, 424/725

(56) References Cited

U.S. PATENT DOCUMENTS

| | | | |
|---|---|---|---|
| 4,698,360 A | 10/1987 | Masquelier | 514/456 |
| 4,923,855 A | 5/1990 | Jensen | 514/188 |
| 4,954,492 A | 9/1990 | Jensen | 514/188 |
| 5,194,615 A | 3/1993 | Jensen | 546/5 |
| 5,607,965 A * | 3/1997 | Kondo et al. | |
| 5,912,363 A | 6/1999 | Nafisi-Movaghar et al. | 549/399 |
| 6,086,910 A | 7/2000 | Howard et al. | 424/442 |
| 6,099,854 A | 8/2000 | Howard et al. | 424/440 |
| 6,299,896 B1 * | 10/2000 | Cooper et al. | |

OTHER PUBLICATIONS

Angiosperm http://www.search.eb.com/bol/topic?eu=120804&sctn=10&pm=1.*

Lefavi, et al., "Lipid–Lowering Effect of a Dietary Chromium (III)–Nicotinic Acid Complex in Male Athletes," *Nutrition Research* 13:239–249, 1993.

Mertz, Walter "Chromium in Human Nutrition: A Review," *American Institute of Nutrition*, 626–633, 1993.

Leighton, et al., "Plasma Polyphenols and Antioxidants, Oxidative DNA Damage and Endothelial Function in a Diet and Wine Intervention Study in Humans," *Drugs Exp. Clin. Res.*, 25(2–3):133–141, 1999.

Rifici et al., "Red Wine Inhibits the Cell–Mediated Oxidation of LDL and HDL," *J. Am. Col. of Nutr.*, 18:(2)137–143, 1999.

Ruf JC, "Wine and Polyphenols Related to Platelet Aggregation and Atherothrombosis," *Drugs Exp. Clin. Res.*, 25:(2–3)125–131, 1999.

Talpur, et al., "Effects of Chromium, Grape Seed Extract, and Zinc Alone and In Combination On Blood Pressure of Spontaneously Hypertensive Rats," *Journal of the American College of Nutrition*, 18(5):35, 1999.

Yamakoshi, et al., "Proanthocyanidin–rich Extract From Grape Seeds Attenuates the Development of Aortic Atherosclerosis in Cholesterol–fed Rabbits," *Atherosclerosis* 142:139–149, 1999.

Preuss, et al., "Effects of Niacin–Bound Chromium and Grape Seed Proanthocyanidin Extract on the Lipid Profile of Hypercholesterolemic Subjects: A Pilot Study," *Journal of Medicine*, 31(5–6):227–246, 2000.

Talpur, et al., "Effects of Chromium and Grape Seed Extract on the Lipid Profile of Hypercholesterolemic Patients," *The FASEB J.*, 14(4):503, Mar. 15, 2000.

\* cited by examiner

*Primary Examiner*—Christopher R. Tate
*Assistant Examiner*—Randall Winston
(74) *Attorney, Agent, or Firm*—Marshall, Gerstein & Borun

(57) ABSTRACT

Methods and compositions for reducing cholesterol levels are provided which involve administering an effective daily dosage of proanthocyanidin and niacin-bound chromium to a subject.

1 Claim, No Drawings

METHODS AND COMPOSITIONS FOR REDUCING CHOLESTEROL LEVELS USING A PROANTHOCYANIDIN AND NIACIN-BOUND CHROMIUM COMPLEX

This application claims the benefit of U.S. Provisional Patent Application Serial No. 60/199,076, filed Apr. 20, 2000, the disclosure of which is hereby incorporated by reference.

BACKGROUND OF THE INVENTION

This invention relates generally to methods and compositions for reducing blood cholesterol levels in a subject.

According to recent information from the American Heart Association, an estimated 100,870,000 American adults have total cholesterol levels in the borderline-high risk range of 200 mg/dl to 239 mg/dl. There are 40,600,000 American adults living with high-risk cholesterol levels of 240 mg/dl or more. There are many risk factors that can indicate a propensity to have high levels of cholesterol, such as age, weight, health conditions such as diabetes, smoking, gender, race and ethnicity. Elevated blood cholesterol levels are associated with potentially deadly conditions of the heart and blood vessels, such as atherosclerosis, coronary artery insufficiency and stroke.

Atherosclerosis is the most common cause of death and serious morbidity in the Western world. Atherosclerosis is one of three morphologically distinct forms of arteriosclerosis. Arteriosclerosis is the hardening of the arteries due to their thickening and loss of elasticity. Atherosclerosis occurs when irregularly distributed lipid deposits form in the inner coating of the vessels of the elastic arteries, such as the aorta, carotid and iliac, or the large and medium-sized muscular arteries, such as the coronary and popliteal. These lipid deposits, called atheromatous plaques, cause fibrosis and calcification which leads to coronary heart disease and myocardial infarction. The plaques are comprised of cells, macrophages and other leukocytes, a connective tissue extra-cellular matrix and intracellular and extracellular lipid deposits. The progression of atherosclerosis can be slowed by reducing the plasma cholesterol and cholesterol LDL levels.

Hypercholesterolemia, or elevated blood cholesterol levels due to concentration of cholesterol in the cells and plasma, is also prevalent in the American population. Elevated total and LDL cholesterol levels are considered cardiovascular risk factors for coronary heart disease and myocardial infarction.

Cholesterol is the most abundant steroid in cell membranes and is essential to the growth and viability of cells. Cholesterol is classified as a lipid and forms lipoproteins, or complexes of cholesterol and protein. There are four major categories of lipoproteins: chylomicrons, very low density lipoproteins (VLDL), low density lipoproteins (LDL), and high density lipoproteins (HDL). Chylomicrons transport some dietary cholesterol and mostly triglycerides from the intestines to the adipose tissue (also known as fat) and the liver. VLDLs transport cholesterol and triglycerides made by the liver to adipose and other tissues. LDL is a byproduct consisting of apolipoprotein and cholesterol that remains after the fat cells have removed the triglycerides from the VLDL. LDLs transport cholesterol to the peripheral tissues (cells outside the liver and intestine) and regulate the endogenous cholesterol levels therein. LDL is often referred to as the "bad cholesterol" because high levels increase the risk of developing arteriosclerosis and hypercholesterolemia. HDL, known as the "good cholesterol," transports cholesterol from the peripheral tissues (and arterial walls) to the liver. HDLs operate as good cholesterol because they oppose LDLs. It is thought that high levels of HDL can reverse the negative effects of LDL activity. The primary site of cholesterol synthesis is in the liver, although some cholesterol is synthesized in the intestines. The liver's function in this pathway is to remove the cholesterol from the blood. Plasma LDL is the primary source of cholesterol in peripheral tissues, which do not synthesize cholesterol de novo. LDL is taken into these cells via endocytosis at LDL receptor cites. The molecular genetics and cellular biology of the LDL receptor has been characterized by Goldstein and Brown. The LDL receptor is essential to cholesterol metabolism. When cholesterol is abundant inside the cell, there is no synthesis of LDL receptors, and thus cholesterol uptake from plasma cholesterol is blocked. The absence of the LDL receptor leads to hypercholesterolemia and atherosclerosis.

Free radical activity produces oxidized LDL. When macrophages take up oxidized LDL, they form foam cells which form the atheromatous plaques, described above, in the larger blood vessels. As these plaques cause fibrosis and calcification which lead to coronary heart disease and myocardial infarction, oxidized LDL levels are important indicators of patients with a disease propensity. Yamakoshi et al., "Proanthocyanidin-Rich Extract From Grape Aortic Atherosclerosis in Cholesterol-Fed Rabbits," *Atherosclerosis*, 142:139–149 (1999).

Wine has been shown to protect LDLs from lipid peroxidation. Specifically, red wine inhibits cell-mediated oxidation of LDL, whereas white wine does not seem to produce similar results. Rifici et al., "Red Wine Inhibits the Cell-Mediated Oxidation of LDL and HDL," *J. Am. Coll. Nutr.*, 18:137–143 (1999). This inhibition is believed to be caused by the antioxidant activity of proanthocyanidins responsible for the color of red wine. Nuttall et al., "An Evaluation of the Antioxidant Activity of a Standardized Grape Seed Extract," Leucoselect, *J. Clin. Pharm. Ther.*, 23:385–389 (1998); see also, Yanakoshi et al., "Proanthocyanidin-Rich Extract from Grape Seeds Attenuates the Development of Aortic Atherosclerosis in Cholesterol-Fed Rabbits," *Atherosclerosis*, 142:139–149 (1999).

Proanthocyanidins comprise a group of polyphenolic bioflavonoids ubiquitously found in fruits and vegetables. They are the most common type of tannins found in fruits and vegetables, and are present in high amounts in the seeds and skins of grapes. Proanthocyanidins consist of polymers of the flavan-3-ol units (+)-catechin, (−)-epicatechin and (−)-epicatechin 3-O-gallate linked by C4–C8 or C4–C6 bonds. Some proanthocyanidins carry galloyl residues linked to the C-3 alcoholic function of the flavan-3-ol units. Proanthocyanidins have been the subject of considerable interest because of their broad pharmacologic activity and therapeutic potential. Chen et al., "Antioxidative Activity of Natural Flavonoids is Governed by Number and Location of Their Aromatic Hydroxyl Groups," *Chem. Phys. Lipids*, 79:157–163 (1996). The biological and medicinal properties of the proanthocyanidins have been extensively reviewed, see, Rice-Evans et al., "Structure-Antioxidant Activity Relationships of Flavonoids and Phenolic Acids," *Free Rad. Biol. Med.*, 20:933–956 (1996). Purified proanthocyanidin compositions of this invention may be isolated or derived from a variety of plant sources according to known methods or may be produced synthetically. Proanthocyanidins are found in the fruit and seeds of a wide variety of fruit plants including but not limited to strawberry, blueberry and grapes. Proanthocyanidins are also present in large quantities in maritime pine bark, oak wood, black and green tea and in cocoa powder.

Chromium deficiency has also been linked to the development of atherosclerosis. Schroeder et al., "Chromium Deficiency as a Factor in Atherosclerosis," *J. Chron. Dis.*, 23:123–142 (1970); Newman et al., "Serum Chromium and Angiographically Determined Coronary Artery Disease," *Clin. Chem.*, 24:341–544 (1978); Simonoff, "Chromium Deficiency and Cardiovascular Risk," *Cardiovas. Res.*, 18:591–6 (1984); Simonoff et al., "Low Plasma Chromium in Patients with Coronary Artery and Heart Disease," *Biol. Trace Elem. Res.*, 6:431–439 (1984); Cote et al., "Hair Chromium Concentration and Coronary Artery Diseases in Canada, France, and Italy," *Nutr. Res. Suppl. I*, 356–359 (1985). Chromium (Cr) is necessary for insulin function as it is the biologically active component of glucose tolerance factor (GTF). GTF also contains nicotinic acid and is responsible for insulin activity. Oral chromium supplementation can lower cholesterol and triglyceride levels and increase HDL levels. For example, a double-blind study of thirty-four male athletes examined the effects of a dietary GTF-like supplement comprised of trivalent chromium nicotinic acid ingested daily for eight weeks. Lefavi et al., "Lipid-Lowering Effect of a Dietary Chromium (III)-Nicotinic Acid Complex in Male Athletes," *Nutrition Research*, 13:239–249 (1993). The supplement was accompanied by body building training while dietary conditions remained status quo. Serum lipid analyses were performed pre and post supplement after twelve hours of fasting and one hour of an athletic challenge. All pre-supplement values for insulin, glucose, total cholesterol, LDL, and HDL levels were with normal ranges. The data showed no change between groups regarding their insulin concentration and glucose tolerance, markers of insulin function. However, the lipid parameters reflected the lipid-lowering effects of this supplement similar to those observed for organic Cr compounds. Chromium's influence on the various dyslipidemias is not consistent from study to study. Offenbacher et al., "Beneficial Effect of Chromium-rich Yeast on Glucose Tolerance and Blood Lipids in Elderly Subjects," *Diabetes*, 29:919–925 (1980); Urberg et al., "Hypocholesterolemic Effects of Nicotinic Acid and Chromium Supplementation," *J. Fam. Prac.*, 27:603–606 (1988); Roeback et al., "Effects of Chromium Supplementation on Serum High-density Lipoprotein Cholesterol Levels in Men Taking Beta Blocker," *Ann. Intern. Med.*, 115:917–924 (1991); Press et al., "The Effects of Chromium Picolinate on Serum Cholesterol and Apolipoprotein Fractions in Human Subjects," *West. J. Med.*, 152:41–45 (1990); Abraham et al., "The Effects of Chromium Supplementation on Serum Glucose and Lipids in Patients With and Without Non-Insulin-Dependent Diabetes," *Metab.*, 41:768–771 (1992). There is also conflicting data showing that chromium has little effect. Uusitupa et al., "Chromium Supplementation in Impaired Glucose Tolerance of Elderly: Effects on Blood Glucose, Plasma Insulin, C-peptide, and Lipid Levels," *Br. J. Nutr.*, 68:209–216 (1992). The variance in the data may be explained by the variance in chromium forms (ligands), dosages, and patients' age, gender, and health status.

Cholesterol levels are measured by withdrawing blood from a patient and performing standard blood chemistry tests thereon. Pharmaceuticals exist to treat elevated cholesterol levels but the majority cause significant side-effects, such as liver problems. For example, patients with hypercholesterolemia are usually started on one of three lipid-lowering therapeutic agents: (1) bile acid-binding resins, (2) niacin; or (3) 3-hydroxy-3-methylglutaryl-coenzyme A (HMG-CoA) reductase inhibitors. These drugs cause respectively: (1) constipation, gastric discomfort, nausea, hemorrhoidal bleeding; (2) arrhythmias, peptic ulcer disease, glucose intolerance, hepatic dysfunction; and (3) abnormal liver function and myositis. If these agents, normally prescribed as the first line of therapy are not successful, fibric acid derivatives like gemfibrozil are often administered. There are also side-effects with this class of drugs, such as lithogenicity of bile, nausea, abnormal liver functions and myositis. There remains a need for an effective method to reduce blood cholesterol levels without creating other medical complications. The present invention fulfills theses needs and provides further related advantages.

SUMMARY OF THE INVENTION

The present invention resides in methods and compositions to reduce cholesterol levels in a subject by administering an effective amount of proanthocyanidin and niacin-bound chromium (NBC).

Specifically, the invention provides for methods of reducing cholesterol levels in subjects that have been identified as having elevated cholesterol levels by administering proanthocyanidin and NBC in amounts effective to reduce cholesterol levels. The subject is preferably a human but could be a domestic animal or other subject with elevated cholesterol levels. While those of ordinary skill in the art can vary the daily dosages based upon the weight of the subject, the preferred daily dosage of proanthocyanidin is about 100–400 mg with the preferred daily dosage of NBC about 2–6 mg. The daily dosages of proanthocyanidin and NBC are preferably delivered orally, intravenously or by other method of delivery that one of skill in the art would employ. The proanthocyanidin is preferably grape seed proanthocyanidin extract (GSPE).

The invention also provides for compositions of proanthocyanidin and NBC. These compositions are preferably comprised of dosage units effective to reduce cholesterol levels, such as about 100–400 mg of proanthocyanidin per day and about 2–6 mg of NBC per day. A further preferred embodiment of the invention provides that proanthocyanidin is GSPE.

Other features and advantages of the present invention should become apparent from the following detailed description of the invention, which illustrate the principles of the invention.

DETAILED DESCRIPTION OF THE INVENTION

An embodiment of the present invention involves administering proanthocyanidin and NBC to a subject as part of a suitable composition designed to be consumed by the subject. The method involves consumption of the composition by the subject, preferably as a regular treatment; e.g., daily. The composition contains an amount of proanthocyanidin and NBC sufficient to reduce blood cholesterol levels in the subject. The composition may be consumed by many known methods, such as orally or intravenously. As used herein "cholesterol" lowered by the practice of the invention includes total cholesterol, LDL, oxidative LDL, HDL, triglycerides combined or any of those components thereof individually.

Proanthocyanidin compositions such as those described herein are preferably proanthocyanidin from grapes, with grape skin and grape seeds being preferred sources. Purified proanthocyanidin may be obtained from methods such as those described in U.S. Pat. No. 5,912,363, the disclosure of which is incorporated herein by reference. A particularly preferred purified proanthocyanidin composition available as a standardized water-ethanol extract from red grape seeds for use according to this invention is available as a grape seed proanthocyanidin extract (GSPE) known under the ActiVin® brand available from InterHealth Nutraceuticals, Inc., Benicia, Calif. A compositional analysis of the ActiVin® brand grape seed proanthocyanidin extract shows a content comprising (by weight) 54% proanthocyanidin dimer, 13% proanthocyanidin trimer, 7% proanthocyanidin tetramer, and 6% monomer and other flavonoids. Because it is believed that the prophylactic and therapeutic activities of the purified proanthocyanidin compositions of the invention are primarily associated with the low molecular weight ($DP_2$ to $DP_4$) oligomeric content of the purified proanthocyanidin compounds preferred purified proanthocyanidin compositions comprise at least 50% and more preferably greater than 70% by weight $DP_2$ to $DP_4$ oligomeric proanthocyanidins.

The NBC compositions such as those described herein are also known as chromium-nicotinate GTF material, polynicotinate and are preferably available commercially as ChromMate® from InterHealth Nutraceuticals, Inc., Benicia, Calif. The ChromMate® brand of NBC is made from at least an alkali metal salt of nicotinic acid, a trivalent chromium salt and adjuvants. The composition and process for synthesizing the ChromMate® brand of NBC is disclosed in U.S. Pat. Nos. 5,194,615, 4,954,492 and 4,923,855, incorporated herein by reference. In general, a dissociable form of alkali metal, like an alkali metal hydroxide and nicotinic acid are combined to form the alkali metal salt of nicotinic acid. This salt is then reacted with trivalent chromium salt to yield the chromium-nicotinate GTF material (NBC). The ChromMate® brand of NBC can also be synthesized by reacting the alkali metal salt of nicotinic acid, obtained from other sources as known in the art, with the chromium salt. These reactions can be made with minimum temperature controls, from about 5° C. to about 60° C., and are usually performed in a polar solvent system, like an aqueous or alcohol solvent. The crude chromium-nicotinate can be washed, in water or other solvent in which the ChromMate® brand of NBC is insoluble, to remove any soluble compounds or dried at about 10° C. to about 150° C. at less than 100% relative humidity. ChromMate® brand of NBC is believed to be comprised of at least a substantial portion of a trinicotinic chromium complex, where 1 mg of ChromMate® brand of NBC contains 100 µg of elemental chromium. A representative structure of ChromMate® brand of NBC is shown in U.S. Pat. No. 5,194,615.

According to an embodiment of the invention, a synergistic effect is achieved, when appropriate doses of GSPE and NBC (GSPE/NBC) are administered, that results in lower cholesterol levels than either GSPE or NBC alone or additively in the subject. The GSPE/NBC can be delivery by capsule, tablet or liquid or any other convenient form consistent with oral or injectable modes of administration. The composition can include inert ingredients or diluents, like starch or talc; other pharmaceutical ingredients of the sort often contained in over-the-counter analgesic remedies, such as caffeine, provided that adverse chemical reactions do not occur; and a barrier coating of a standard inert composition capable of separating the active ingredients. As one skilled in the art would appreciate, the GSPE/NBC can be administered by various methods, including orally or by injection.

EXAMPLE 1

According to this example, a study was performed primarily to determine whether a combination of GSPE, NBC and zinc monomethionine could enhance insulin sensitivity and lessen oxidative damage over a prolonged period of time in a strain of rats usually employed when studying the benefits of caloric restriction. Ancillary to the study, data related to cholesterol levels was also obtained. The study took place over one year with 104 rats (obtained from breeding Fischer 344 rats with Brown Norway rats), half of which were fed a baseline diet and served as the control group; and half of which received the baseline diet plus daily dosages of 250 ppm of GSPE, 5 ppm of NBC and 18 ppm of elemental zinc contained in a composition of zinc monomethionine sold as OptiZinc® by InterHealth Nutraceuticals of Benicia, Calif. These rat dosages correlate to 200 mg of GSPE, 4 mg of NBC and 15 mg of elemental zinc in human (as humans weigh approximately 175 times that of the average rat). Freirich et al., "Comparison of Toxicity of Anticancer Agents in Mouse, Rat, Hamster, Dog, Monkey and Man," *Cancer Chem. Report*, 50:219–239 (1996).

The blood chemistries of these rats were tested in both arms by routine laboratory procedures at approximately five weeks of age and from the heart at the conclusion of the experiment and four hours after food removal. All statistics were performed by one-way analysis of variance (ANOVA) using repeated measures except statistics relating to blood pressure and body weight, which were examined by two-way variance of diet and time. Where a significant effect of diet was detected by ANOVA ($p<0.05$) the Dunnett's test was used to establish the statistical significance between the differences between means.

There were no significant differences in the total cholesterol, HDL and triglycerides values between the groups as reflected by the comparison of the average±SEM baseline measurement with those taken at the conclusion of the study. However, this is likely to be caused by the fact that this strain of rats was not a good model for studying cholesterol changes in such a short time frame. Typically, one would expect blood pressure to be the first sign that compositions such as these are having a therapeutic effect, whereas significant changes in cholesterol levels could take a year and a half or more to observe in this rat model. Thus, for the focus of this study, these rats were sufficient to measure insulin sensitivity and oxidative damage observed by statistically significant variance in blood pressure but not cholesterol levels.

EXAMPLE 2

According to this example, hypercholesterolemic human patients with cholesterol levels of 210–300 mg/dl were examined in a randomized, double-blind, placebo-controlled study. Four groups, of ten patients each, received a twice-daily dosage of either: (1) a placebo; (2) 100 mg of grape seed proanthocyanidin extract (GSPE) marketed under the brand name ActiVin® by InterHealth Nutraceuticals of Benicia, Calif.; (3) 2 mg of chromium-nicotinate known as NBC and marketed under the brand name ChromeMate® by InterHealth Nutraceuticals (containing 200 µg of elemental chromium); or (4) 2 mg of NBC (containing 200 µg of elemental chromium) plus 100 mg of GSPE. The patients received the compositions for a period of two months, but were instructed not to otherwise change their lifestyles or treatment therapy, if applicable.

Total cholesterol, LDL, HDL, and triglyceride levels were measured for the patients in each group at the beginning, at the end of one month, and at the end of the two months. To assess oxidized LDL, autoantibodies to Ox-LDL were employed as they are an indirect measure of oxidized LDL.

The autoantibodies were estimated using a nonisotopic ELISA technique as described by Ridket et al., "Inflammation, Aspirin and the Risk of Cardiovascular Disease in Apparently Healthy Men," *New Engl. J. Med.*, 336:973–979 (1997) and Bui et al., "Auto Antibody Titers to Oxidized Low-Density Lipoprotein in Patients with Coronary Atherosclerosis," *Am. Heart J.*, 131:663–667 (1996). LDL obtained commercially from PerImmune Co. (Rockville, Md.) was oxidized in the presence of $CuCl_2$ at room temperature (5 mmol/l). The comparison between the electropheretic mobility of Ox-LDL relative to that of native LDL was 4.0. Wells of microliter ELISA plates (Immunon 2, Dynatech Laboratories, Inc., Chantilly, Va.) were coated with either native LDL or Ox-LDL and then blocked with 2% Bovine Serum Albumin (Sigma Chem Co, St Louis, Mo.) at room temperature for one hour. Thereafter, a 1:10 dilution of sera was incubated for one hour at 37° C. At the conclusion of the hour, horseradish peroxidase-conjugated rabbit antihuman immunoglobulin (IgG) was added to each well at a 1:1000 dilution. A substrate of orthophenylenediamine and hydrogen peroxide in citric acid and sodium phosphate buffer solution (pH 5.0) were used to bring the reaction to completion. After twenty minutes, the reaction was stopped with sulfuric acid (2 mol/l) and an absorbance reading was taken at 490 nm, as measured in a micro-ELISA plate reader (Dynatech Laboratories, Inc, Chantilly Va.). Autoantibody titers were calculated by subtracting binding to native LDL from binding to Ox-LDL and expressed as optical density (OD).

Statistical significance was set at $p<0.05$. A two-way analysis of variance (ANOVA), time and supplement grouping determined significance. The Dunnett t-test determined the statistical significance between means when a significant effect was detected by ANOVA. Dunnet et al., "A Multiple Comparison Procedure for Comparing Several Treatments with Control," *J. Am. Stat. Assoc.*, 50:1096–1121 (1955).

At the end of the two months, thirty-eight patients remained in the study. One patient from the combination group withdrew on day six due to a reaction from migraine-triggering foods that caused sinusitis, otitis media, and the recurrence of migraines. The other patient that withdrew was part of the placebo group and withdrew at the end of month one without complaint.

There were few adverse events reported. Three patients from the NBC group, 1 patient from the combination group, and four in the placebo group presented gastrointestinal symptoms. The patients taking chromium reported adverse events included one report of heartburn, diarrhea, abdominal distension, and insomnia and one report of intestinal gas; both of which reports were designated as mild and resolved by study end. One case of insomnia was reported in the combination GSPE/NBC group. In the placebo group, there was one report of intestinal gas, increased appetite, intermittent LUQ pain, and a metallic taste. Other placebo subjects reported leg cramps, insomnia, and increased appetite. Thirty-two patients did not report any adverse events.

At the initialization of the study, the total cholesterol levels of the four groups, comparing the average ± SEM baseline with the eight week values were,: placebo 251±7.6 as compared to 241±12.3 mg/dl, GSPE 245±9.7 as compared to 238±9.8 mg/dl, NBC 267±4.4 as compared to 244±11.5 mg/dl, and GSPE/NBC combination 250±9.0 as compared to 215±11.2 mg/dl. While NBC alone tended to decrease the concentration of total cholesterol as compared to the placebo, the combination of GSPE/NBC caused a significant decrease in the total cholesterol levels as compared to the baseline.

LDL cholesterol concentrations reflect similar data to that seen for total cholesterol. At the end of eight weeks, the respective readings were: placebo 160±9.6 as compared to 155±8.9 mg/dl, GSPE 160±10.2 as compared to 157±9.1 mg/dl, NBC 181±10.4 as compared to 162±12.5 mg/dl, and GSPE/NBC 174±9.6 as compared to 147±11.6 mg/dl. The LDL cholesterol levels significantly decreased as compared to the baseline upon administration of the combination of GSPE/NBC.

HDL values, at the end of eight weeks, showed no statistically significant differences on any of the regimes as compared to the baseline readings. Comparing the baseline and eight week values: placebo 55.0±4.0 as compared to 56.2±4.5 mg/dl, GSPE 48.0±6.5 as compared to 47.6±7.0 mg/dl, NBC 48.9±5.7 as compared to 48.5 ±5.7 mg/dl, and combination GSPE/NBC 36.7±2.8 as compared to 37.8±3.2 mg/dl.

Triglyceride concentrations were also studied. The changes over eight weeks in triglyceride concentrations as compared to the baseline were: placebo—30.6 mg/dl, GSPE—24.8 mg/dl, NBC—3.7 mg/dl and GSPE/NBC—69.8 mg/dl.

In addition, data relating to percent differences over the eight weeks were obtained regarding autoantibodies to oxidized LDL, which enable the estimation of the most atherogenic form of cholesterol: placebo—17.3%, GSPE—30.7%, NBC—10.4% and GSPE/NBC—44.0%.

According to the blood chemistry, determined by withdrawing blood from each patient, administration of the GSPE/NBC combination significantly decreased total cholesterol and LDL levels when compared to administration of the placebo. HDL levels and triglyceride concentrations did not differ significantly among the groups. In this basically normotensive population, the blood pressure changes also were not significantly different. These results suggest that administration of the combination of GSPE/NBC significantly decreases total cholesterol and LDL levels in a subject. The patients in the study described herein showed no significant adverse side effects or reactions to the GSPE/NBC combination. Preferred daily dosages for an adult are from about 200–600 μg of NBC and from about 100–400 mg GSPE. Other dosages can be extrapolated using conventional weight to composition conversions.

The pharmaceutical compositions according to this embodiment of the invention can be in any convenient form suited to the intended mode of administration such as, for example, capsule, liquid, tablet, lozenge, or gum. The composition can include inert ingredients or diluents, such sugar or other inert ingredients commonly used in food products.

Although the invention has been disclosed in detail with reference to a preferred embodiments, those skilled in the art will appreciate that additional methods of administering proanthocyanidin and NBC and compositions comprising the same can be made without departing from the scope of the invention.

What is claimed is:

1. A method for reducing cholesterol levels in a subject, the method comprising identifying a subject with elevated cholesterol levels, and administering proanthocyanidin and niacin-bound chromium to the subject in amounts effective to reduce cholesterol levels in the subject, wherein the amount of proanthocyanidin is about 100–400 mg per day and the amount of niacin-bound chromium is about 2–6 mg per day.

* * * * *